United States Patent

Harris et al.

[11] Patent Number: 6,052,464
[45] Date of Patent: Apr. 18, 2000

[54] TELEPHONE SET HAVING A MICROPHONE FOR RECEIVING OR AN EARPIECE FOR GENERATING AN ACOUSTIC SIGNAL VIA A KEYPAD

[75] Inventors: Daryl Harris, Chicago; Kevin D. Kaschke; David L. Bond, both of Hoffman Estates, all of Ill.

[73] Assignee: Motorola, Inc., Schaumburg, Ill.

[21] Appl. No.: 09/087,124

[22] Filed: May 29, 1998

[51] Int. Cl.[7] .................................................. H04M 1/00
[52] U.S. Cl. .............................................................. 379/433
[58] Field of Search .................................. 379/433, 430, 379/428; 455/90, 515

[56] References Cited

U.S. PATENT DOCUMENTS

| | | | |
|---|---|---|---|
| 5,446,789 | 8/1995 | Loy et al. | 379/433 |
| 5,721,787 | 2/1998 | Neibaur et al. | |
| 5,729,604 | 3/1998 | Van Schyndel | |

OTHER PUBLICATIONS

Motorola Trade Booth brochure for Booth #5139, "Experience The Future . . . iDEN @CTIA," Mar. 19, 1998.
U.S. application No. 08/957,276, filed Oct. 24, 1997, Assignee: Motorola, Inc.

*Primary Examiner*—Jack Chiang
*Attorney, Agent, or Firm*—Kevin D. Kaschke; Paul J. Bartusiak

[57] ABSTRACT

A telephone set (10) comprises a first housing (12), a second housing (14), a rotate (54) or a slide (34) mechanism, a microphone (16), an earpiece (18) and a keypad (20). The rotate (54) or the slide (34) mechanism couples the first housing (12) to the second housing (14) and permits the first housing (12) to be moveable relative to the second housing (14) between a first, closed or contracted, position (22) and a second, open or expanded, position (24). The microphone (16) is carried by the first housing (12) and is adapted to convert an acoustic input signal (26) into an electric input signal (28). The earpiece (18) is carried by the second housing (14) and is adapted to convert an electric output signal (30) into an acoustic output signal. The keypad (20) is carried by one of the first housing (12) and the second housing (14) and has an aperture (32) extending therethrough. In a first embodiment, the earpiece (18) is disposed behind the keypad (20) essentially opposite to the aperture (32) of the keypad (20) when the keypad (20) is carried by the second housing (14) to permit the acoustic output signal generated by the earpiece (18) to be ported through the aperture (32) of the keypad (20). In a second embodiment, the microphone (16) is disposed behind the keypad (20) essentially opposite to the aperture (32) of the keypad (20) when the keypad (20) is carried by the first housing (12) to permit the acoustic input signal (26) to be ported through the aperture (32) of the keypad (20) to be received by the microphone (16). The present invention advantageously permits the telephone set (10) to be made shorter by integrating the microphone (16) or the earpiece (18) with the keypad (20).

35 Claims, 11 Drawing Sheets

TELEPHONE SET HAVING A MICROPHONE FOR RECEIVING OR AN EARPIECE FOR GENERATING AN ACOUSTIC SIGNAL VIA A KEYPAD

CROSS REFERENCE TO RELATED APPLICATIONS

The present patent application is related to copending application having Ser. No. 09/087,125, (Attorney's docket number CE01302R) filed by Kevin D. Kaschke and David L. Bond on the same date herewith and assigned to the assignee of the present invention.

FIELD OF THE INVENTION

The present invention generally relates to telephone sets and, more particularly to, a telephone set having a microphone for receiving an acoustic signal through an aperture in a keypad or having an earpiece for generating an acoustic signal through an aperture in a keypad.

BACKGROUND OF THE INVENTION

Telephone sets, such as portable cellular or cordless telephone sets, are well known in the art. Telephone sets typically include a microphone, an earpiece, a keypad and a loudspeaker. The microphone converts an acoustic input signal into an electric input signal. The earpiece converts an electric output signal into an acoustic output signal. Typically, a person positions the telephone set against the person's head to Sign the microphone with the person's mouth and to align the earpiece with the person's ear to permit the person to speak the acoustic input signal into the microphone and to listen to the acoustic output signal generated by the earpiece. When a telephone set permits a person to speak and listen to another party at the same time this is known as full duplex voice communications. The keypad permits a person to enter data, such as a phone number, into the telephone set. The loudspeaker converts an electric output signal into an acoustic output signal. The loudspeaker generates an acoustic output signal at a volume level much higher than volume level of the acoustic output signal generated by the earpiece to permit a person to listen to the acoustic signal generated by the loudspeaker when the telephone set is positioned far away from the person's ear. The volume level of the acoustic output signal from loudspeaker is set at a high enough level so that the person's ear can hear the level of the acoustic output signal generated by the loudspeaker, but not so high as to damage the person's hearing. Use of the loudspeaker is sometimes referred to as a handsfree mode of operation. The handsfree mode may be used when a person holds the telephone set in one hand while entering a phone number into the keypad with the other hand. The handsfree mode may also be used when the person needs to see or touch writable displays while listening to the loudspeaker. The handsfree mode may also be used when several listeners wish to listen to the same conversation over the loudspeaker.

As advances in technology have permitted telephone sets to be made smaller in size and lighter in weight, the available space for implementing necessary features such as microphones and earpieces becomes limited. One such trend in miniaturization is evident when viewing the following U.S. Pat. Nos.: U.S. Pat. No. Des. 369,162-Nagele et al. (single piece housing design), known as a DynaTAC (TM) phone model, U.S. Pat. No. Des. 365,817-Mischenko et al. (main housing with an additional flap housing rotating to cover or uncover a keypad on the main housing), known as a Micro-TAC (TM) phone model, and U.S. Pat. No. Des. 369,598-Nagele et al. (clam shell housing design), known as a StarTAC (TM) phone model, all being made and sold by Motorola, Inc. Each of these phone models has an earpiece, a display, a keypad and a microphone carried by one or more housings and arranged on the one housing or on two housings in the order stated here when the two housings are in their opened position during use. The earpiece and the microphone are located at opposite ends of the one or more housings during use to maximize the distance between the earpiece and the microphone and to align the earpiece and the microphone with a person's ear and mouth, respectively, while minimizing the total length of the one or more housings. However, the advantage of having easily accessible features, such as a large keyed or large display, contrasts with the availability of limited space on the one or more housings of the telephone set to place such features.

U. S. Pat. No. 5,721,787 teaches one approach towards miniaturizing a radio device while maintaining a large keypad by placing a loudspeaker behind the keypad. An acoustic output signal generated by the loudspeaker is ported through openings in the keypad into free space outside the radio device. The openings are appropriately aligned and routed to minimize the amount of water intruding through the openings. However, although this configuration provides a place to put a relatively large loudspeaker, the earpiece, the display, the keypad and the microphone carried by the housing are still arranged on the housing in the order stated here. Therefore, the total length of the housing remains unchanged by placing the loudspeaker behind the keypad.

Further, a problem with loudspeakers is that the high volume level of the acoustic output signal may be too loud when the radio device is placed too close to a person's ear. To address this problem, U.S. Pat. No. 5,729,604 teaches a radio device designed so that the loudspeaker will not generate the acoustic signal when the radio device is placed near the person's ear to prevent the person's ear front experiencing a painful acoustic shock by accidentally receiving a high level acoustic output signal from the loudspeaker. In U. S. Pat. No. 5,729,604, the radio device has a proximity sensor to automatically switching between the earpiece and the loudspeaker responsive to the handset being brought into proximity with the person's ear.

Accordingly, there is a need for a telephone set that is shorter, smaller and more integrated while providing the necessary functions of a microphone and an earpiece.

DETAILED DESCRIPTION OF THE PREFERRED EMBODIMENTS

Figure 5:
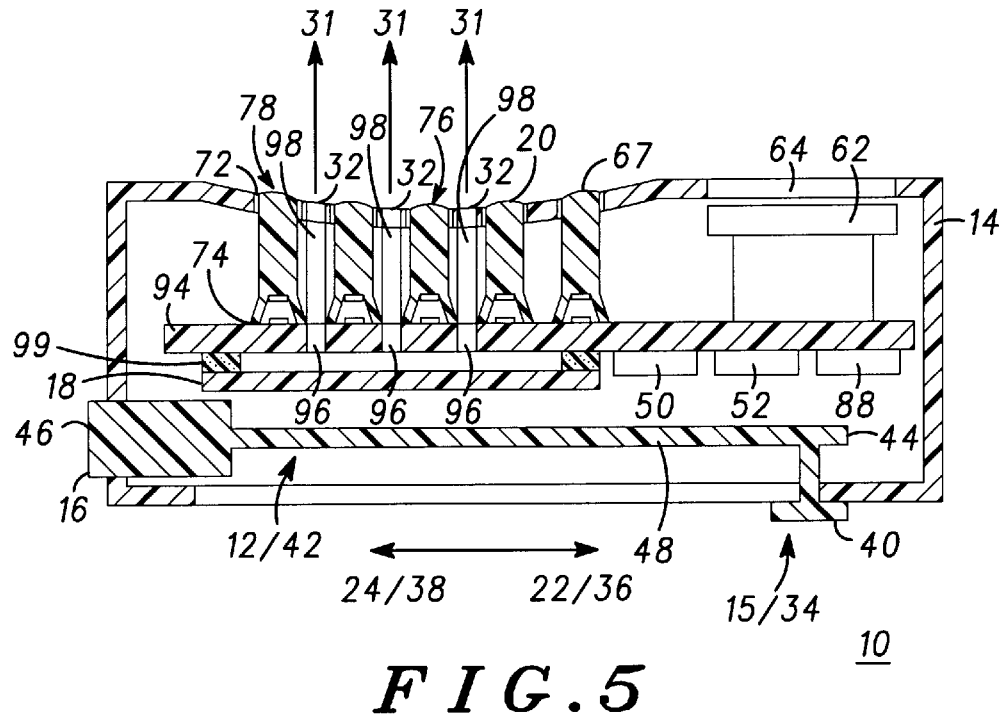
FIG. 5 illustrates a cross sectional view of the telephone set as shown in FIGS. 1 and 2.
Figure 6:
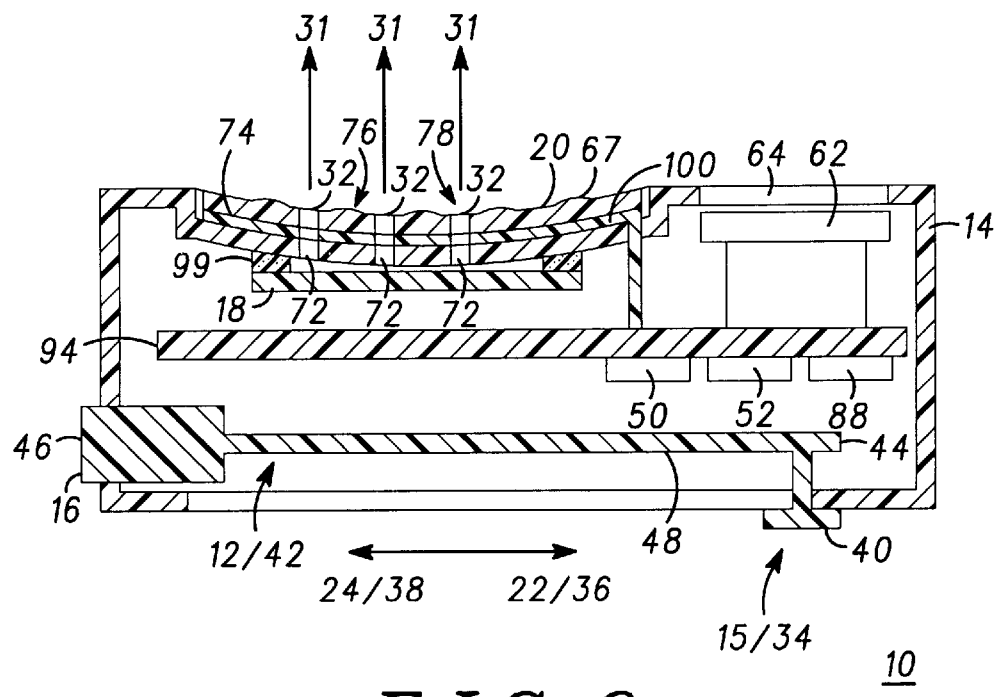
FIG. 6 illustrates an alternate cross sectional view of the telephone set as shown in FIGS. 1 and 2.
Figure 7:
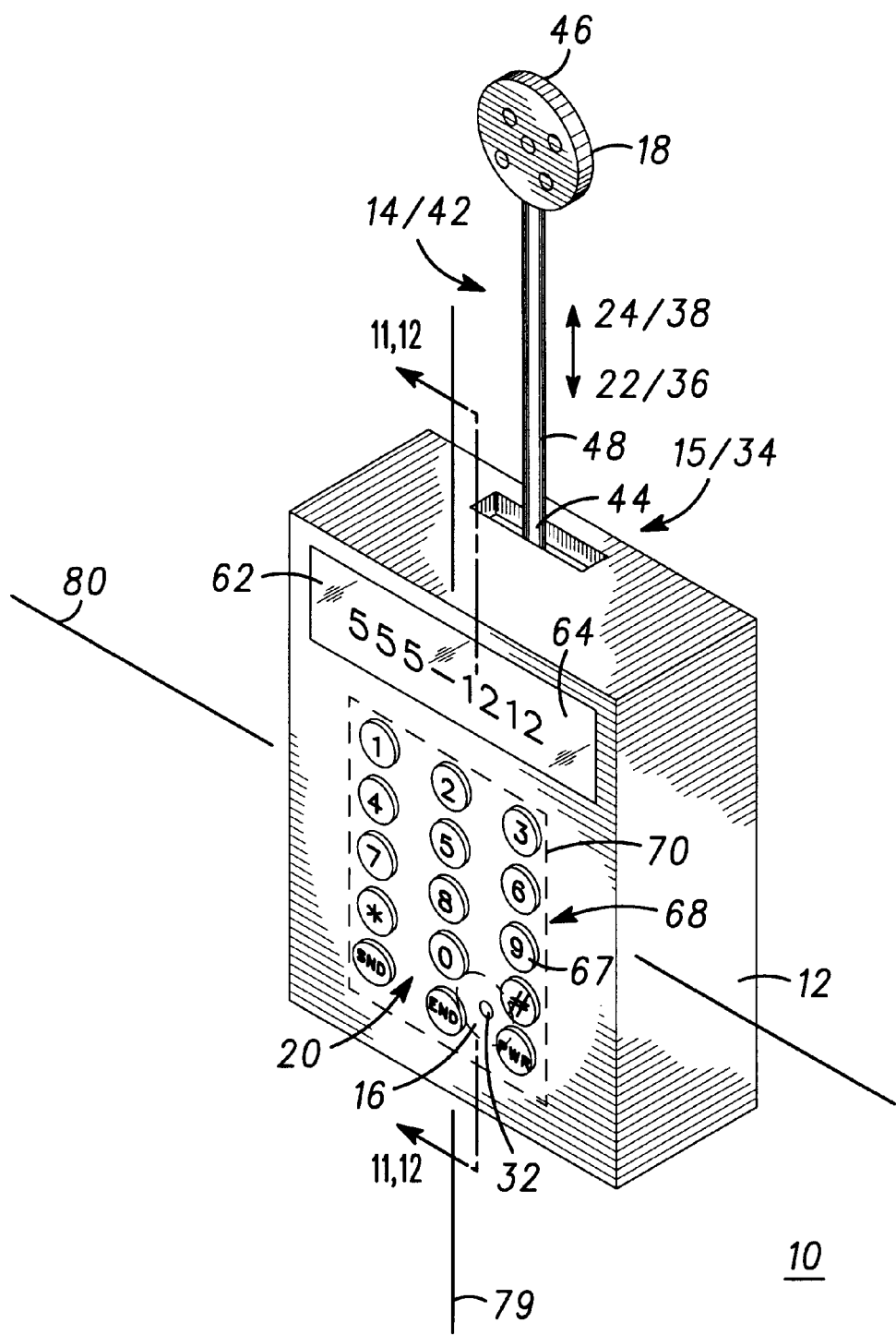
FIG. 7 illustrates a right side, front side and top side perspective view of a telephone set having an microphone for receiving an acoustic signal through an aperture in a keypad in accordance with a second embodiment of the present invention and having a sliding mechanism coupling a first housing and a second housing.

The present specification generally describes two alternative embodiments of a telephone set 10. FIGS. 1–6 illustrate the first embodiment of the telephone set 10 wherein FIGS. 5 and 6 illustrate alternate cross sectional views of the first embodiment of the telephone set 10. FIGS. 7–12 illustrate the second embodiment of the telephone set 10 wherein FIGS. 11 and 12 cross sectional views of the second embodiment of the telephone set 10. FIG. 13 illustrates an electrical block diagram showing circuitry that is in each of the telephone sets as shown in FIGS. 1–12. Although particular features are shown in particular figures, these particular feature combinations are provided for example only and any feature of one figure may be deleted from the one figure, exchanged with a feature of another figure or added to another figure to create multiple feature combinations.

Referring generally to FIGS. 1–12, the telephone set 10 generally comprises a first housing 12, a second housing 14, an attachment mechanism 15, a microphone 16, an earpiece 18 and a keypad 20. The first housing 12 and the second housing 14 may have any shape such as round, oval or square and may be of any size such as narrow or wide. The attachment mechanism 15 is coupled to the first housing 12 and the second housing 14 and is adapted to permit the first housing 12 to be moveable relative to the second housing 14 between a first position 22 and a second position 24. The microphone 16 is carried by the first housing 12 and adapted to convert an acoustic input signal 26 into an electric input signal 28. The earpiece 18 is carried by the second housing 14 and is adapted to convert an electric output signal 30 into an acoustic output signal 31. The keypad 20 is carried by one of the first housing 12 and the second housing 14. The keypad 20 has an aperture 32 extending through the keypad 20.

Figure 1:
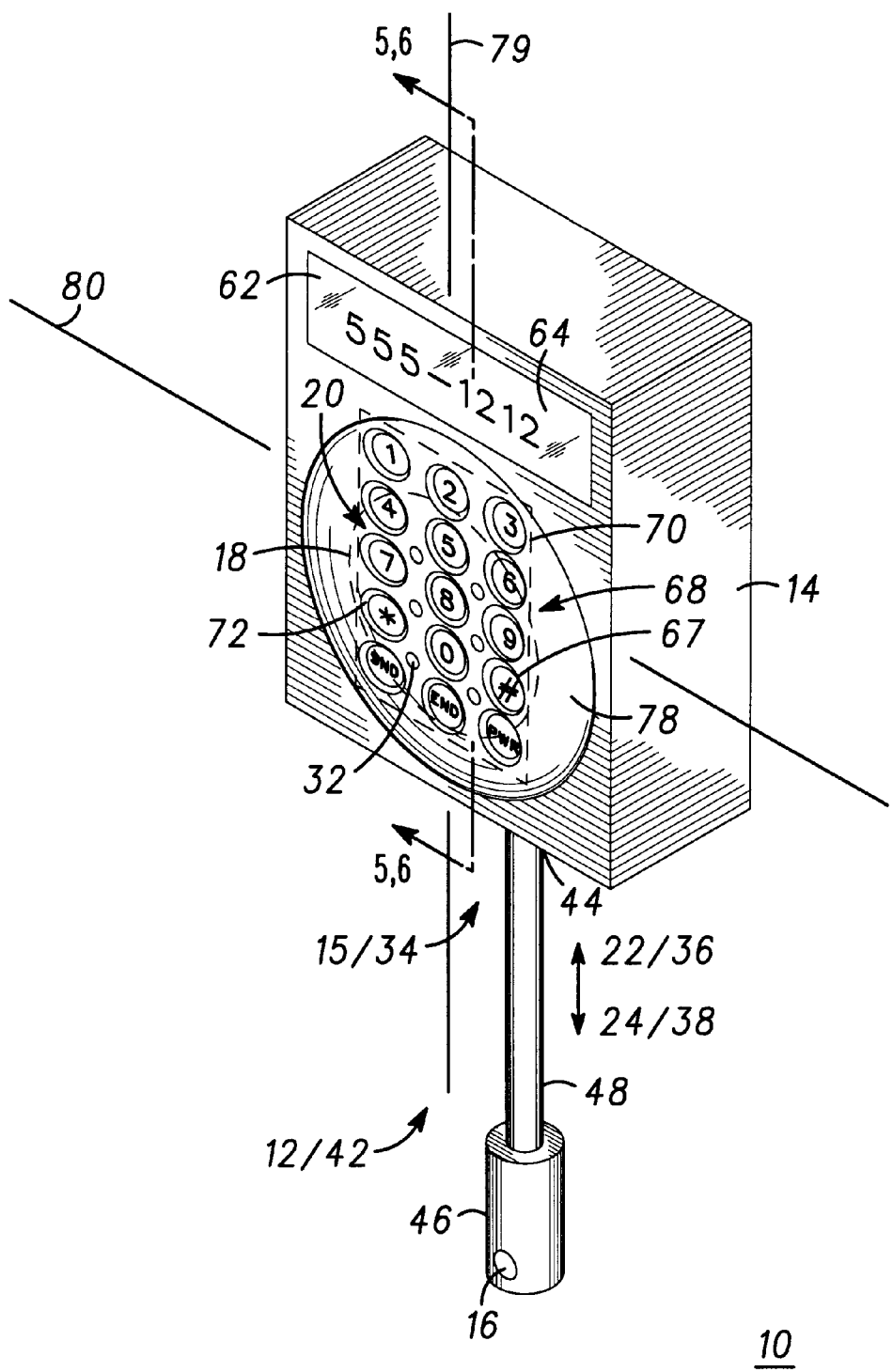
FIG. 1 illustrates a right side, front side and top side perspective view of a telephone set having an earpiece for generating an acoustic signal through an aperture in a keypad in accordance with a first embodiment of the present invention and having a sliding mechanism coupling a first housing and a second housing.
Figure 2:
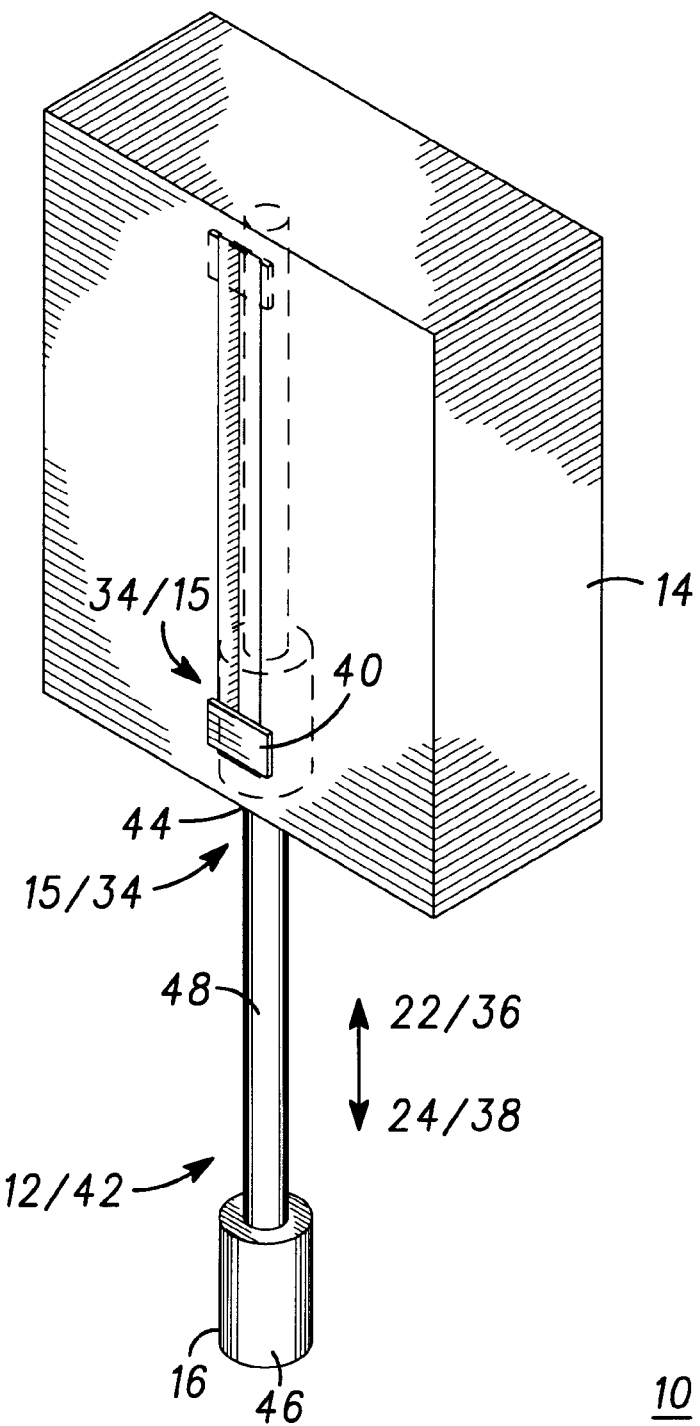
FIG. 2 illustrates a left side, back side and top side perspective view of the telephone set as shown in FIG. 1.
Figure 3:
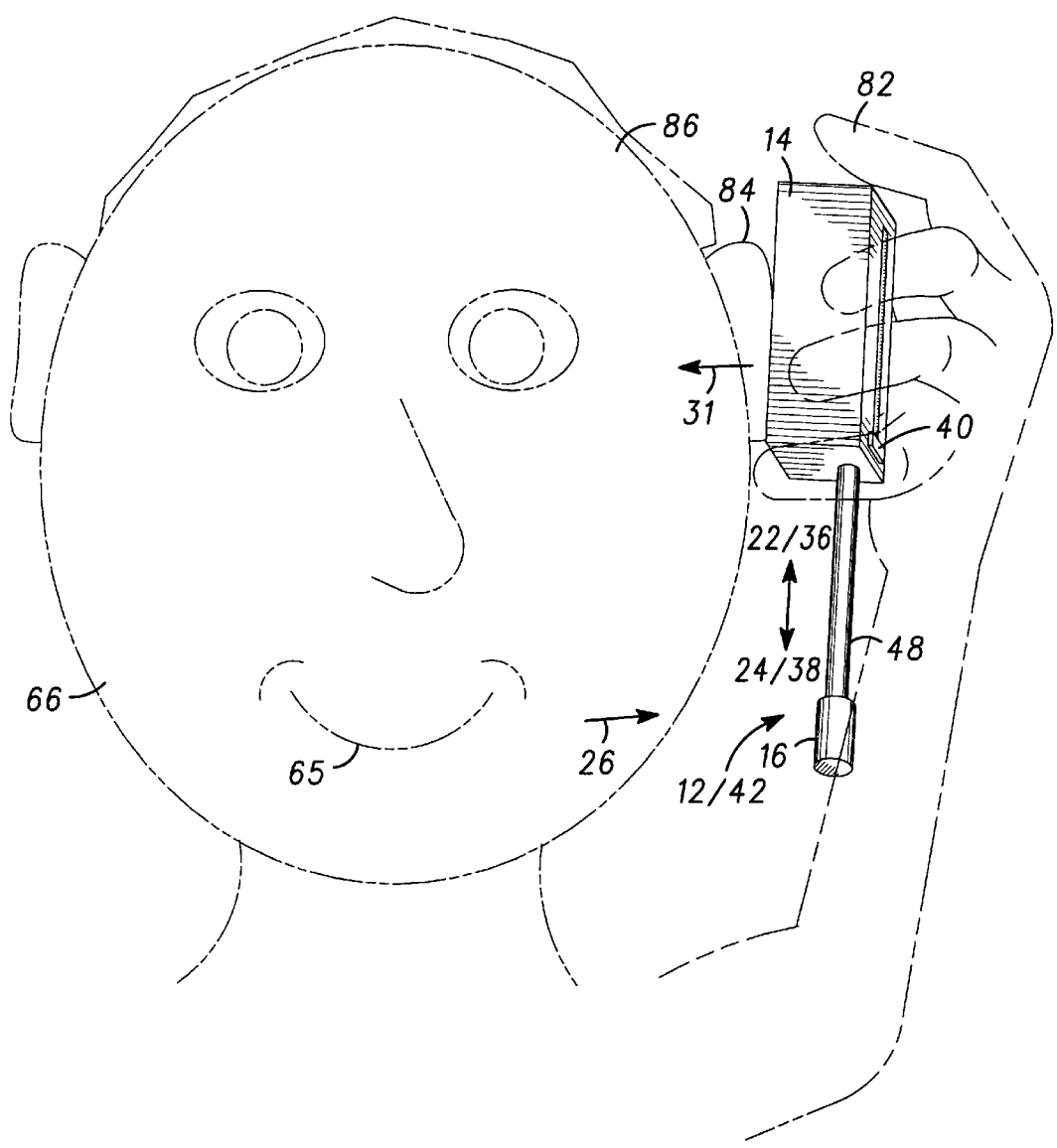
FIG. 3 illustrates a right side, back side and bottom side perspective view of the telephone set as shown in FIGS. 1 and 2 when held against a person's head.

As shown in FIGS. 1–6, according to the first embodiment of the present invention, the earpiece 18 is disposed behind the keypad 20 and is disposed essentially opposite to the aperture 32 of the keypad 20 when the keypad 20 is carried by the second housing 14 to permit the acoustic output signal 31 generated by the earpiece 18 to be ported through the aperture 32 of the keypad 20. As shown in FIG. 3, a person holds the telephone set 10 against the person's head so that the earpiece behind the keypad aligns with the person's ear so that the person can listen to the acoustic output signal 31 generated by the earpiece 18. By positioning the earpiece 18 behind the keypad 20, the telephone set 10 is advantageously made shorter than conventional telephone sets. The difference in length between the telephone set 10 shown in FIGS. 1–6 and conventional telephone sets is at least the extra length of the housing to accommodate an earpiece above a display in a conventional telephone set. With present day earpiece technology, the total length of the first embodiment of the telephone set 10 is made shorter by a distance of about 30 mm.

Figure 8:
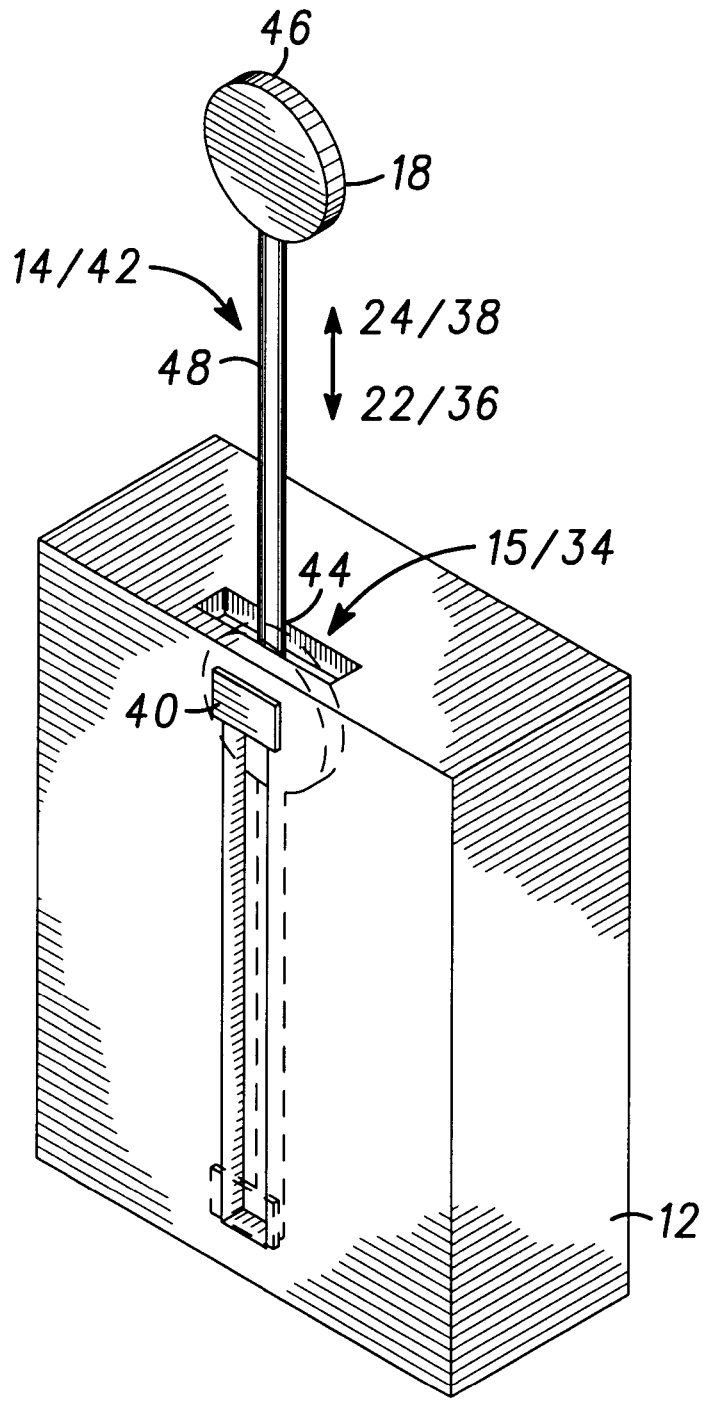
FIG. 8 illustrates a left side, back side and top side perspective view of the telephone set as shown in FIG. 7.
Figure 9:
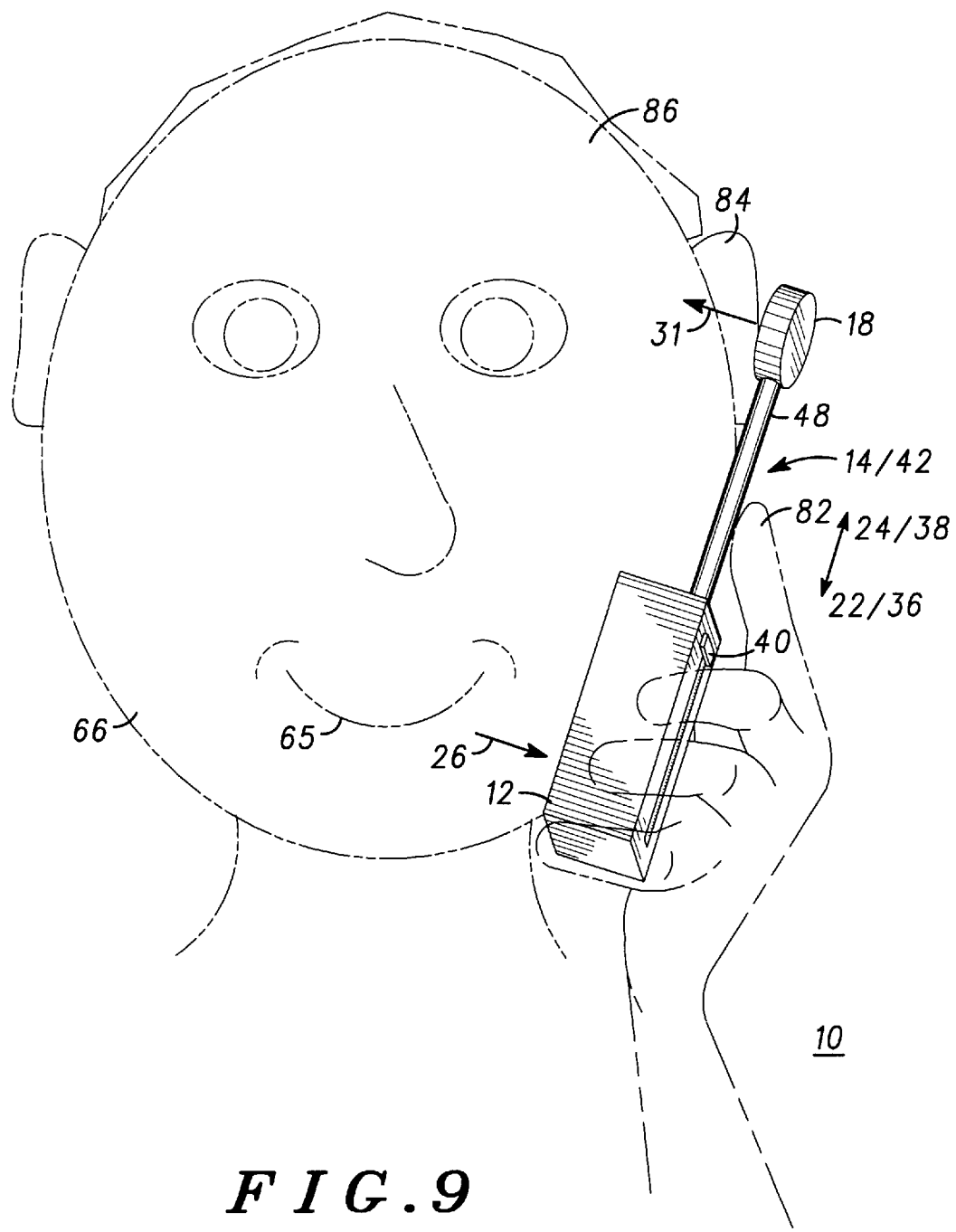
FIG. 9 illustrates a right side, back side and bottom side perspective view of the telephone set as shown in FIGS. 7 and 8 when held against a person's head.

As shown in FIGS. 7–12, according to the second embodiment of the present invention, the microphone 16 is disposed behind the keypad 20 and is disposed essentially opposite to the aperture 32 of the keypad 2C when the keypad 20 is carried by the first housing 12 to permit the acoustic input signal 26 to be ported through the aperture 32 of the keypad 20 to be received by the microphone 16. As shown in FIG. 9, a person holds the telephone set against the person's head so that the microphone behind the keypad aligns with the person's mouth 65 so that the person can generate the acoustic input signal 26 by speaking for receipt by the microphone 16. By positioning the microphones 16 behind the keypad 20, the telephone set 10 is advantageously made shorter than conventional telephone sets. The difference in length between the telephone set 10 shown in FIGS. 7–12 and conventional telephone sets is at least the extra length of the housing to accommodate an microphone below a keypad in a conventional telephone set. With present day earpiece technology, the total length of the second embodiment of the telephone set 10 is made shorter by a distance of about 10 mm.

Referring to FIGS. 1,2, 3, 5 and 6 and FIGS. 7, 8, 9, 11 and 12, the attachment mechanism 15 is preferably a slide mechanism 34 adapted to permit the first housing 12 to slide relative to the second housing 14 between the first position 22 and the second position 24. With the slide mechanism 34, the first position 22 comprises a contracted position 36 and the second position 24 comprises an expanded position 38. In the contracted position 36 the first housing 12 and the second housing 14 are in their respective stowed positions to permit the telephone set 10 to be carried or stored. In the expanded position 38 the first housing 12 and the second housing 14 are in their respective unstowed positions to permit the telephone set 10 to be used. The slide mechanism 34 is preferably moved manually, but may also be moved semiautomatically or automatically. To manually move the first housing 12 between the contracted position 36 and the expanded position 38, a person's finger 82 slides a button 40 which is connected to the appropriate housing (i.e. first housing or second housing) being moved. Alternatively, a person may move the appropriate housing by grabbing the appropriate housing near the microphone to manually move the appropriate housing between the contracted position 36 and the expanded position 38. To semiautomatically move the appropriate housing, a person releases a latch (not shown) to release the force of a bias spring (not shown) to move the appropriate housing to the contracted position 36 or the expanded position 38 and manually moves the appropriate housing to the expanded position 38 or the contracted position 36, respectively.

As shown in FIGS. 1–6 and FIGS. 7–12, the first housing 12 and the second housing 14, respectively, preferably comprises an elongated rod 42 having a proximal end 44 and a distal end 46. The elongated rod 42 preferably has a length less than or equal to a length of the other housing. As shown in FIGS. 1, 2, 3, 5 and 6 and FIGS. 7, 8, 9, 11 and 12, the slide mechanism 34 is preferably a telescoping mechanism permitting the proximal end 44 of the elongated rod 42 to slide in and out of the second housing 14 and the first housing 12, respectively. The telescoping mechanism may have one or more telescoping elongated rods 42. With the telescoping mechanism, the elongated rod is constructed to be substantially stiff to encourage the elongated rod to telescope easily in and out of the other housing without binding or bending. But, even in this case the elongated rod may be allowed to bend somewhat to prevent damage to the elongated rod in the event that the elongated rod is accidentally bent by dropping the telephone set 10, sitting on the telephone set 10, etc. The elongated rod 42 is preferably disposed along a longitudinal axis 79 of the center of the other housing, but may be disposed off the longitudinal axis 79 of the center of the other housing such as along the side of the other housing.

As shown in FIGS. 1–6 the microphone 16 is disposed at the distal end 46 of the elongated rod 42 in order to maximize the distance between the microphone and the earpiece. As shown in FIGS. 7–12, the earpiece 18 is disposed at the distal end 46 of the elongated rod 42 in order to maximize the distance between the microphone and the earpiece. The elongated rod 42 around the earpiece 18 is preferably substantially flat, but may be shaped like an earplug such as that similar for use with a hearing aid or shaped like a private earpiece corded extension similar to that provided with Motorola's StarTAC (TM) phone or Sony's Walkman (TM) stereo to provide for optimal acoustic coupling between the earpiece 18 and the person's ear 84.

Preferably, the elongated rod 42 comprises an antenna 48. The connections between the antenna 48 and a transmitter 50 and a receiver 52 and the connections between one of the microphone 16 and the earpiece 18 and one of the transmitter 50 and the receiver 52, respectively, are routed through the elongated rod 42. Hence, a combination of the elongated rod 42 comprising the antenna 48, one of the microphone 16 and the earpiece 18 being disposed at the distal end 46 of the elongated rod 42 and the other one of the microphone 16 and the earpiece 18 being disposed behind the keypad 20 advantageously provides for a compact, integrated design for the telephone set 10.

Figure 4:
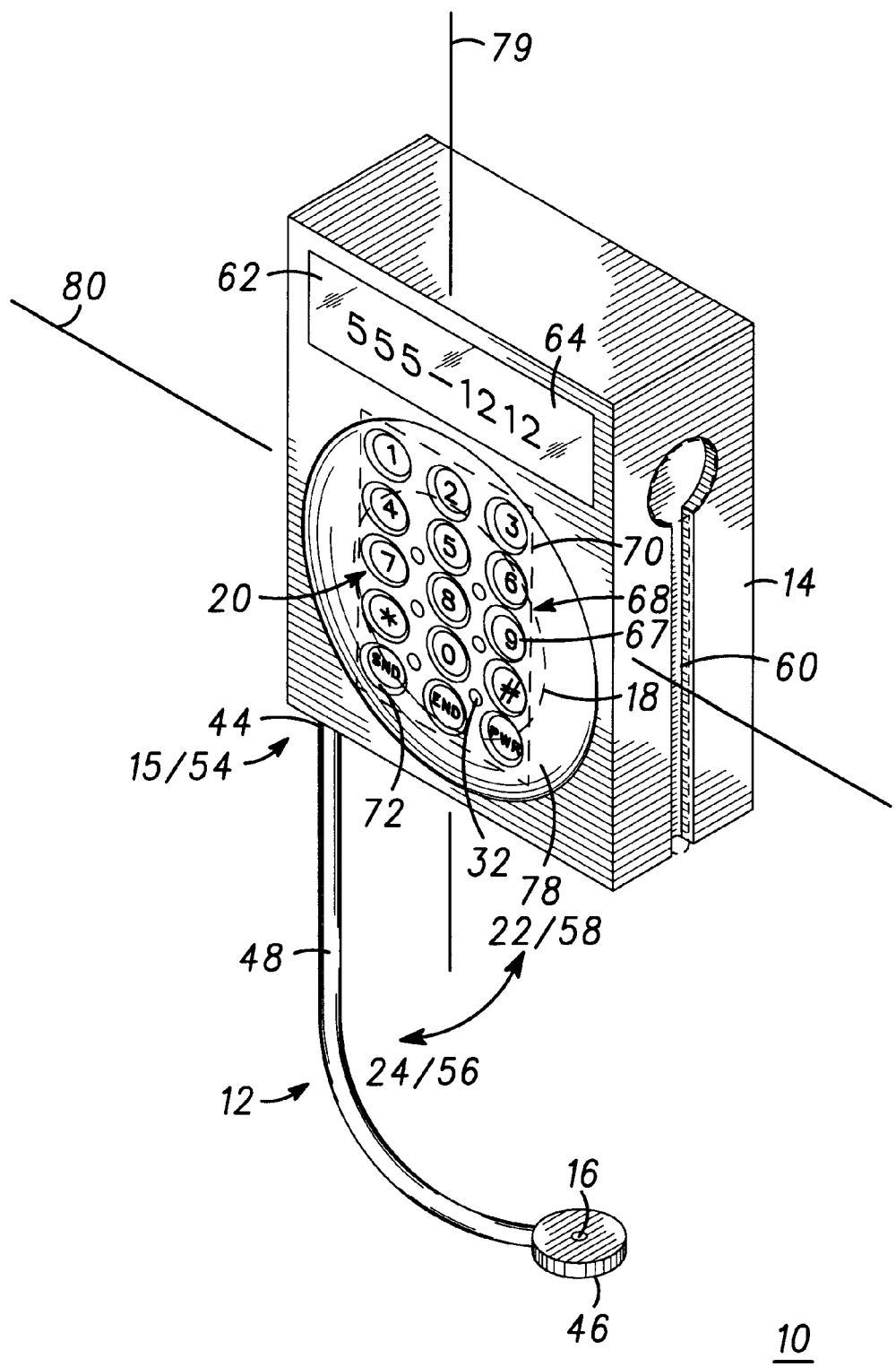
FIG. 4 illustrates a right side, front side and top side perspective view of a telephone set having an earpiece for generating an acoustic signal through an aperture in a keypad in accordance with the first embodiment of the present invention and having a rotate mechanism coupling the first housing and the second housing.
Figure 10:
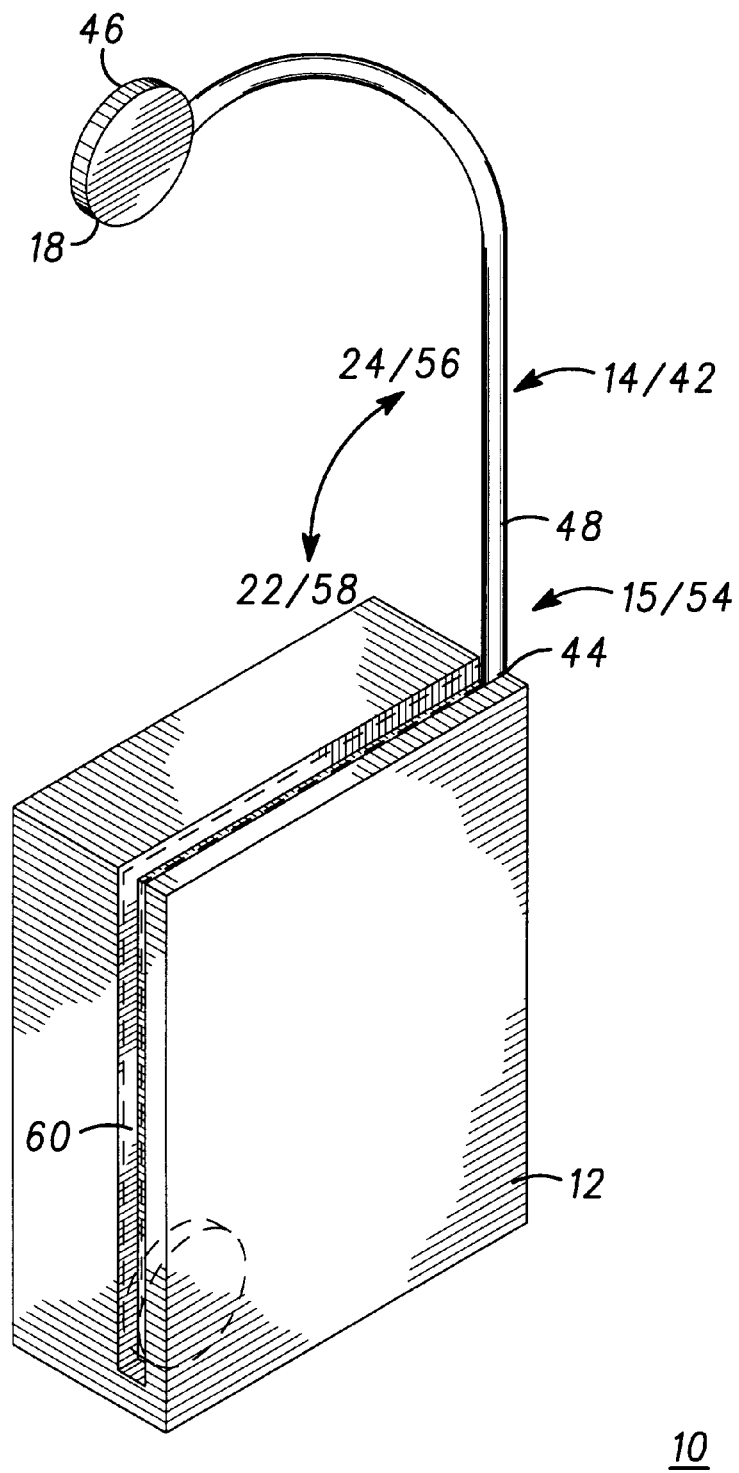
FIG. 10 illustrates a right side, back side and top side perspective view of a telephone set having an microphone for receiving an acoustic signal through an aperture in a keypad in accordance with the second embodiment of the present invention and having a rotate mechanism coupling the first housing and the second housing.

Referring to FIGS. 4 and 10, the attachment mechanism 15 is alternatively a rotate mechanism 54 adapted to permit the first housing 12 to rotate relative to the second housing 14 between the first position 22 and the second position 24. With the rotate mechanism 54, the first position 22 comprises a closed position 58 and the second position 24 comprises an open position 56. In the closed position 58 the first housing 12 and the second housing 14 are in their respective stowed positions to permit the telephone set 10 to be carried or stored. In the open position 56 the first housing 12 and the second housing 14 are in their respective unstowed positions to permit the telephone set 10 to be used for communicating. As shown in FIGS. 4 and 10, the first housing 12 (FIG. 4) or the second housing 14 (FIG. 10) is preferably made to be flexible. The proximal end 44 of the one housing is attached to the outside of the other housing. The distal end 46 of one housing is flexible enough to permit a person to manually rotate or wrap the one housing around the outside of the other housing to position the one housing in the closed position 58. In the closed position 58 the one housing lies in a groove 60 to permit the other housing to have a flush feel and appearance. A detent mechanism (not shown), such as tabs on either housing, for example, hold the wrapped housing in place. Likewise, a person manually removes the distal end 46 of the one housing from the grove by unwrapping the one housing relative to the other housing to position the one housing in the open position 56 relative to the other housing. The wrapped flexible housing may be constructed from a material having a memory effect to hold the housing in the proper position when moved to the open position. As an alternative to the wrapping method, the one housing may be recoiled inside the other housing with the aid of a spring (not shown) exerting a bias force on the one housing in a manner similar to that exerted on a recoiled cord or tape measure, for example. Alternatively, the rotate mechanism 54 may be a stiff mechanism with a hinge mechanism attaching one housing to the other housing. Further, one housing may rotate relative to a perpendicular plane as opposed to a parallel plane of the other housing. FIGS. 3 and 8 are examples of one housing rotating relative to the other housing in a plane parallel to the plane of the other housing. A portable cellular telephone named MicroTAC (TM) or Flip Phone (TM) made by Motorola, Inc. is an example of one housing rotating relative to the other housing in a plane perpendicular to the plane of the other housing.

Referring to FIGS. 1–6, the telephone set 10 preferably comprises a display 62 carried by the second housing 14. According to the first embodiment of the present invention, the keypad 20 also is carried by the second housing 14. Preferably, the keypad 20 is disposed between the display 62 and the microphone 16 when the first housing 12 is moved relative to the second housing 14 to the second position 24. The configuration shown in FIGS. 1–6 shows a unique construction of the first embodiment of the telephone set 10. In addition to making the telephone set 10 shorter, an advantage of positioning the earpiece 18 behind the keypad 20 and below the display 62 is that a person's face oils do not come into contact with a lens 64 covering the display 62 or the keypad 20 because the keypad 20 and the display 62 are positioned above the person's face 66 or near a person's ear 84 instead of near the person's face 66. Face oils have been known to smear a lens to inhibit viewing of a display and also to permeate the material that a keypad is made of to cause a keypad to malfunction.

Referring to FIGS. 7–12, the telephone set 10 alternatively comprises a display 62 carried by the first housing 12. According to the second embodiment of the present invention, the keypad 20 is carried by the first housing 12. Preferably, the display 62 is disposed between the earpiece 18 and the keypad 20 when the first housing 12 is moved relative to the second housing 14 to the second position 24. Note that all of the telephone sets as shown in FIGS. 1–12 have the display 62 positioned above the keypad 20 to permit a person to view the display 62 while entering data into the keypad 20.

As shown in FIGS. 1–12, the keypad 20 comprises a plurality of pushbutton keys 67 arranged in a predetermined pattern 68. The predetermined pattern 68 is shown to be a matrix of pushbutton keys 67 having three columns and five rows. However, any predetermined pattern 68 may be used such as, for example, oval or circular. An outside edge of each of the plurality of pushbutton keys 67 that is located near an outside edge of the predetermined pattern 68 represents a perimeter 70 of the keypad 20. In FIGS. 1 and 4 and FIGS. 7 and 10 the perimeter 70 is represented by a dotted line surrounding the pushbutton keys 67. Preferably, the aperture 32 is disposed within the perimeter 70 of the keypad 20 to provide the most integration.

Preferably, the aperture 32 is disposed between the plurality of pushbutton keys 67 as shown in FIGS. 1, 4,–6 and FIGS. 7, 11 and 12. Placing the aperture 32 between the plurality of pushbutton keys 67 advantageously minimizes any functional interference between the aperture 32 and the pushbutton keys 67. Alternatively, the aperture 32 may disposed along a side of one of the plurality of pushbutton keys 67. In this case, a hole 72 in the housing permitting a pushbutton key to protrude therethrough also acts as the aperture 32 for porting the acoustic signals. The acoustic signals are channeled between a side of the pushbutton key and the hole 72 in the housing. Alternatively, the aperture 32 may extend directly through one of the plurality of pushbutton keys 67. This construction is advantageous when the spacing between or along side the pushbutton keys 67 is tight. In addition, the microphone 16 may be disposed inside a pushbutton key 67 with the aperture 32 extending through the same pushbutton key 67.

Referring to FIGS. 5–6, and 11–12, the keypad 20 has an inside surface 74 disposed essentially opposite to an outside surface 76. The aperture 32 extends between the inside surface 74 and the outside surface 76. The inside surface 74 and the outside surface 76 faces towards and away from, respectively, one of the first housing 12 and the second housing 14 when the keypad 20 is carried by one of the first housing 12 and the second housing 14, respectively. The inside surface 74 of the keypad 20 faces towards one of the microphone 16 and the earpiece 18 when the keypad 20 is carried by one of the first housing 12 and the second housing 14, respectively.

According to the first embodiment of the present invention as shown in FIGS. 1–6, the keypad 20 and the earpiece 18 are carried by the second housing 14. Preferably, at least one of the outside surface 76 of the keypad 20 and the second housing 14 is shaped to form a concave ear cup 78. The concave ear cup 78 is best viewed in FIGS. 5–6. The concave ear cup 78 is concave along a longitudinal axis 79 of the telephone set 10 as shown in cross sectional FIGS. 5–6 and concave along a lateral axis 80 of the telephone set 10 as shown in perspective FIGS. 1 and 4. The concave ear cup 78 advantageously provides a comfortable fit and acoustic seal between a person's ear 84 and the telephone set 10. Hence, the keypad 20 area of the telephone set 10 advantageously doubles as a concave ear cup 78. By contrast to U.S. Pat. No. 5,721,787 which places a loudspeaker behind a keypad, the keypad in that patent does not provide a concave ear cup. Further, the loudspeaker in that patent generates acoustic output signals at too high a level to be used as an ear piece speaker. U.S. Pat. No. 5,729,604 teaches about the dangers of placing a loudspeaker too close to a person's ear and how to prevent damage to a person's ear resulting from high sound levels from a loudspeaker.

In the first embodiment and the second embodiment of the present invention, a person is encouraged to place the keypad 20 on the telephone set 10 near or against the person's head 86 during use. Accidental physical actuation of the plurality of the pushbutton keys 67 may be likely which will cause electrical activation of the plurality of the pushbutton keys 67. Therefore, according to the first embodiment and the second embodiment of the present invention, the telephone set 10 is adapted to prevent accidental activation of the plurality of pushbutton keys 67 provided by a person's ear 84, a person's mouth 65 or a person's head 86.

Figure 11:
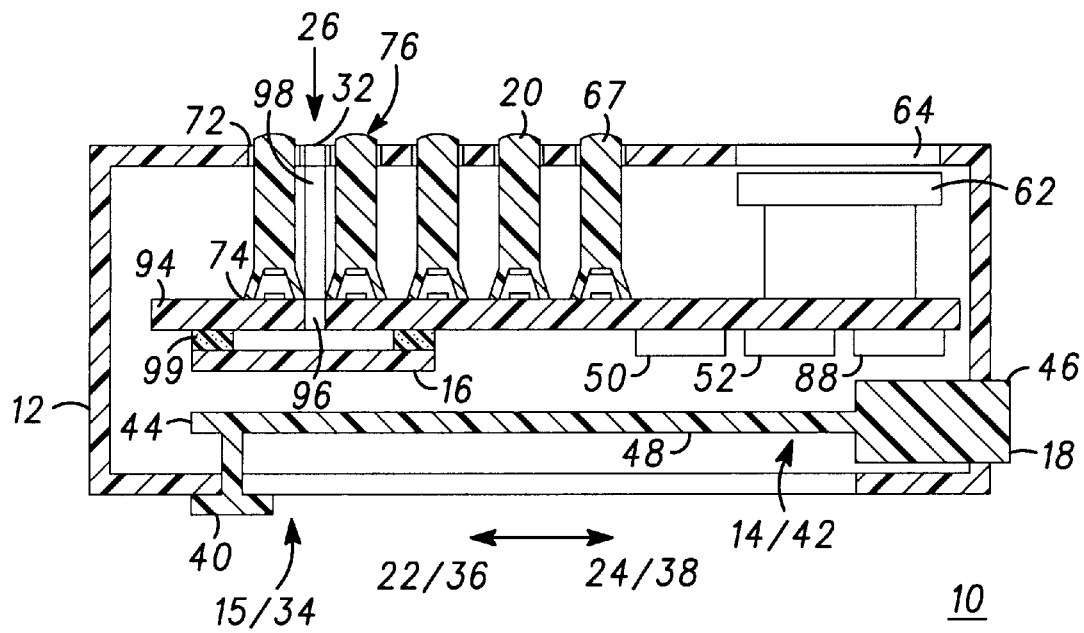
FIG. 11 illustrates a cross sectional view of the telephone set as shown in FIG. 7 and 8.

Referring to FIGS. 5 and 11, the plurality of pushbutton keys 67 are preferably positioned to be substantially flush with the concave ear cup 78 to prevent accidental activation of the plurality of pushbutton keys 67. The height of the pushbutton keys 67 may be slightly above, even with or below the surface of the housing to prevent accidental activation of the plurality of pushbutton keys 67. In the case where the pushbutton keys 67 are slightly above the surface of the housing, the height of the pushbutton key above the housing is less than the amount of vertical travel needed to actuate the pushbutton key to generate a key signal. In this case, the pushbutton keys 67 may be designed with a texture and a shape that provides a comfortable feel against a person's ear 84 or face 66 while preventing accidental activation of the plurality of pushbutton keys 67.

Another way to prevent accidental activation of the plurality of pushbutton keys 67 is to increase the force required to actuate the plurality of pushbutton keys 67. Therefore, the predetermined force required to actuate the pushbutton keys 67 would be designed so that a person's ear 84 or face 66 could not easily actuate the pushbutton keys 67, but a person's finger 82 could easily actuate the pushbutton keys 67.

Still another way to prevent accidental activation of the plurality of pushbutton keys 67 is to use the circuitry shown in FIG. 11. FIG. 11 generally shows the antenna 48, a transmitter 50 coupled to the microphones 16, a receiver 52 coupled to the earpiece 18, a controller 88, a frequency synthesizer 90, the display 62, the keypad 20, a proximity sensor 92, a duplexer 93 and a loudspeaker 95. Each individual element of the circuitry and the connection between the elements, as shown, is known in the art. However, the process carried out by the controller 88 responsive to particular signals or states of the telephone set 10 is considered unique for preventing accidental activation of the plurality of pushbutton keys 67. The controller 88 is coupled to receive a plurality of key input signals generated by the plurality of pushbutton keys 67 when the plurality of pushbutton keys 67 are actuated. In the case of the earpiece 18 being ported through the keypad 20, the controller 88 disables the plurality of key input signals responsive to one of: the ear cup 78 being positioned proximate to the person's ear 84 or the person's head 86 responsive to a signal from the proximity sensor 92, the controller 88 detecting that the earpiece 18 is generating the acoustic output signal 31, the controller 88 detecting that the telephone set 10 is engaged in a telephone call, and an input signal generated by the person manually setting a switch or pressing a particular pushbutton 67 or sequence of pushbuttons 67. Moreover, referring to FIG. 11, the controller 88 also enables the plurality of key input signals responsive to one of: the ear cup not being positioned proximate to the person's ear 84 or the person's head 86 responsive to a signal from the proximity sensor 92, the controller 88 detecting that the earpiece 18 is not generating the acoustic output signal 31, the controller 88 detecting that the telephone set 10 is not engaged in a telephone call, and an input signal generated by the person manually resetting a switch or pressing a particular pushbutton 67 or sequence of pushbuttons 67. Alternatively, in the case of the microphone 16 being ported through the keypad 20, the controller 88 disables the plurality of key input signals responsive to one of: the first housing 12 being positioned proximate to the person's head 86, the microphone 16 receiving the acoustic input signal 26, the controller 88 detecting that the telephone set 10 is engaged in a telephone call, and an input signal generated by the person manually setting a switch or pressing a particular pushbutton 67 or sequence of pushbuttons 67. Likewise, in the same case, the controller 88 also enables the plurality of key input signals responsive to one of: the first housing 12 not being positioned proximate to the person's head 86, the microphone 16 not generating the acoustic output signal 26, the controller 88 detecting that the telephone set 10 is not engaged in a telephone call, and an input signal generated by the person manually setting a switch or pressing a particular pushbutton 67 or sequence of pushbuttons 67. In both the first and the second embodiment of the present invention, the proximity sensor 92 may be an infra red emitter/sensor, for example.

Referring to FIGS. 5 and 11, according to the first embodiment and the second embodiment of the present invention, respectively, the telephone set 10 further comprises a printed circuit board 94 carried by one of the second housing 14 and the first housing 12, respectively. As shown in FIGS. 5 and 11, the printed circuit board 94 is preferably carried between one of the microphone 16 and the earpiece 18 and the keypad 20 when the keypad 20 is carried by one of the first housing 12 and the second housing 14, respectively. The housing, the keypad 20 and the printed circuit board 94 may be constructed as taught in U.S. Pat. No. 5,555,550-Kaschke and U.S. Pat. No. 4,636,593-Novak. In this case, the keypad 20 also has acoustic channels 98 integrally molded into the flexible keypad 20 material to help channel the sound between the holes 96 in the printed circuit board 94 and the holes in the housing. Preferably, a diameter of the channel 98 is a little larger than the hole in the printed circuit board and the hole in the housing to permit proper alignment of these three elements without obstructing the appropriate acoustic input or output signal. Otherwise, without the acoustic channels 98, the dispersion of sound between the painted circuit board 94 and the housing could inhibit the desired acoustic performance of either the earpiece 18 or the microphone 16. A gasket 99 acoustically seals the earpiece 18 or the microphone 16 to the printed circuit board 94.

Figure 12:
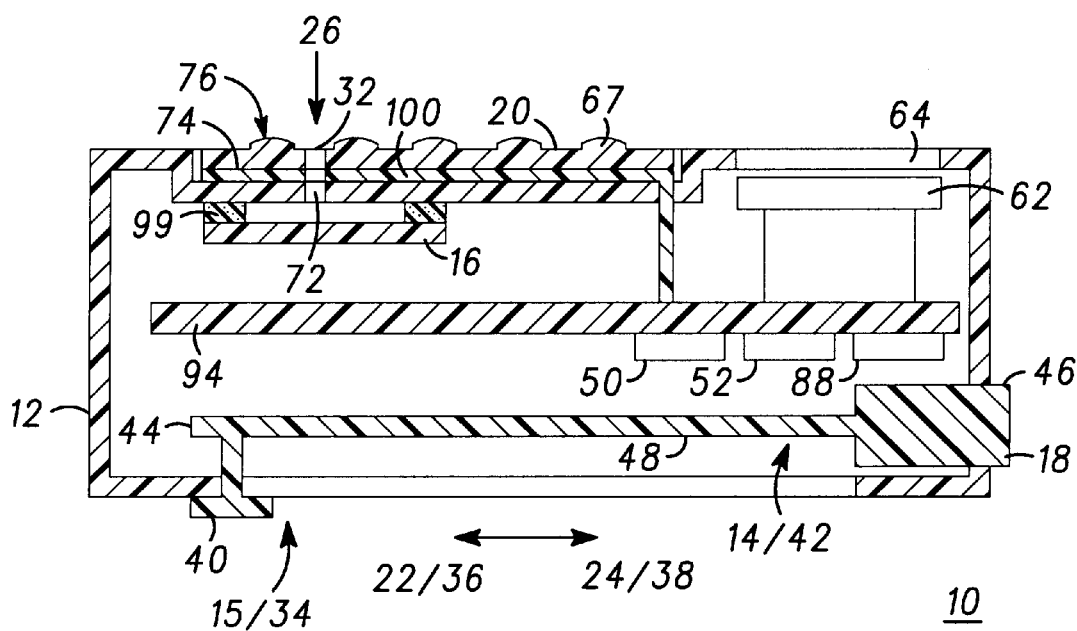
FIG. 12 illustrates an alternate cross sectional view of the telephone set as shown in FIG. 7 and 8.
Figure 13:
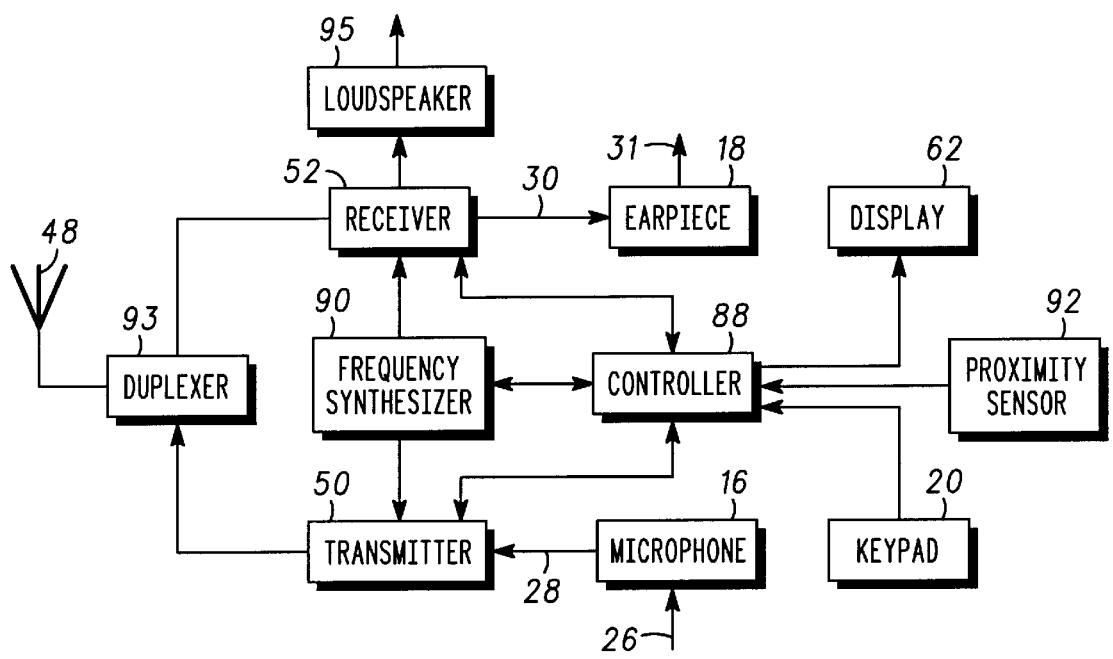
FIG. 13 illustrates an electrical block diagram showing circuitry in the telephone set as shown in FIGS. 1–12.

Referring to FIGS. 6 and 12, alternatively, one of the microphone 16 and the earpiece 18 is carried between the printed circuit board 94 and the keypad 20 when the keypad 20 is carried by one of the first housing 12 and the second housing 14, respectively. The housing, the keypad 20 and the printed circuit board 94 may be constructed as taught in U.S. Pat. No. 4,916,262 Jungles-Butler. In this case, the keypad 20 and a flex circuit 100 having keyboard contacts are known as a membrane keypad and are carried directly on a surface of the appropriate housing. The aperture 32 is routed directly through the keypad 20, the flex circuit 100 and the appropriate housing to either the earpiece 18 or the microphone 16. Therefore, separate acoustic channels 98 are not needed as discussed hereinabove in the previous case. A gasket 99 acoustically seals the earpiece 18 or the microphone 16 to the appropriate housing.

Referring to FIGS. 1–6, in summary of the first embodiment of the present invention, the telephone set 10 comprises the first housing 12, the second housing 14, the attachment mechanism 15 forming the sliding mechanism in the form of the telescoping mechanism or the rotating mechanism, the microphone 16, the earpiece 18, the display 62 and the keypad 20. The first housing 12 forms the elongated rod 42 having the proximal end 44 and the distal end 46. The telescoping or rotating mechanism is coupled to the elongated rod 42 and the second housing 14 and is adapted to permit the elongated rod 42 to slide in and out of the second housing 14 between the contracted position 36 and the expanded position 38 or to wrap around the second housing 14 between the closed position 58 and the open position 56, respectively. The microphone 16 is carried by the distal end 46 of the elongated rod 42 and is adapted to convert the acoustic input signal 26 into the electric input signal 28. The earpiece 18 is carried by the second housing 14 and is adapted to convert the electric output signal 30 into the acoustic output signal 31. The display 62 is carried by the second housing 14. The keypad 20 is also carried by the second housing 14. The keypad 20 is disposed between the display 62 and the microphone 16 when the elongated rod 42 is moved relative to the second housing 14 to the expanded position 38 or the open position 56. The keypad 20 has the inside surface 74 disposed essentially opposite to the outside surface 76. The inside surface 74 and the outside surface 76 facing towards and away from, respectively, the second housing 14. At least one of the outside surface 76 of the keypad 20 and the second housing 14 are shaped to form the concave ear cup 78. The keypad 20 has the plurality of pushbutton keys 67 arranged in the predetermined pattern 68. The outside edge of each of the plurality of pushbutton keys 67 that is located near the outside edge of the predetermined pattern 68 representing the perimeter 70 of the keypad 20. The keypad 20 has the aperture 32 extending through the keypad 20 between the inside surface 74 and the outside surface 76 of the keypad 20. The aperture 32 is disposed within the perimeter 70 of the keypad 20 and the aperture 32 being disposed between the plurality of pushbutton keys 67. The telephone set 10 is adapted to prevent accidental activation of the plurality of pushbutton keys 67 when the outside surface 76 of the keypad 20 is placed against the person's ear 84 or the person's head 86. The earpiece 18 faces the inside surface 74 of the keypad 20 and is disposed essentially opposite to the aperture 32 of the keypad 20 to permit the acoustic output signal 31 generated by the earpiece 18 to be ported through the aperture 32 of the keypad 20. The elongated rod 42 comprises the antenna 48. Where appropriate, other features explained hereinabove also apply to this summary.

Referring to FIGS. 7–12, in summary of the second embodiment of the present invention, the telephone set 10 comprises the first housing 12, the second housing 14, the attachment mechanism 15, the microphone 16, the earpiece 18, the display 62 and the keypad 20. The attachment mechanism 15, either sliding or rotating, is coupled to the first housing 12 and the second housing 14 and is adapted to permit the first housing 12 to be moveable relative to the second housing 14 between the first (closed or contracted) position and the second (open or expanded) position. The microphone 16 is carried by the first housing 12 and is adapted to convert the acoustic input signal 26 into the electric input signal 28. The earpiece 18 is carried by the second housing 14, such as at the distal end 46 of an elongated rod 42, and is adapted to convert the electric output signal 30 into the acoustic output signal 31. The display 62 is carried by the first housing 12. The keypad 20 is also carried by the first housing 12. The display 62 is disposed between the keypad 20 and the earpiece 18 when the first housing 12 is moved relative to the second housing, 14 to the second position 24. The keypad 20 has the inside surface 74 disposed essentially opposite to the outside surface 76. The inside surface 74 and the outside surface 76 facing towards and away from, respectively, the first housing 12. The keypad 20 has the plurality of pushbutton keys 67 arranged in the predetermined pattern 68. The outside edge of each of the plurality of pushbutton keys 67 that is located near the outside edge of the predetermined pattern 68 representing the perimeter 70 of the keypad 20. The keypad 20 has the aperture 32 extending through the keypad 20 between the inside surface 74 and the outside surface 76 of the keypad 20. The aperture 32 is disposed within the perimeter 70 of the keypad 20 and the aperture 32 is disposed between the plurality of pushbutton keys 67. The microphone 16 faces the inside surface 74 of the keypad 20 and is disposed essentially opposite to the aperture 32 of the keypad 20 to permit the acoustic input signal 26 to be ported through the aperture 32 of the keypad 20 to be received by the microphone 16. The second housing 14 formed of an elongated rod 42 comprises the antenna 48. Where appropriate, other features explained hereinabove also apply to this summary.

According to the first embodiment of the telephone set 10 as shown in FIG. 3 the earpiece 18 is behind the keypad 20 in the second housing 14. The second housing 14 and the keypad 20 advantageously provides a large surface area to provide a proper acoustic and comfortable fit between the person's ear 84 and the second housing 14 as well as to block wind and other noise from drowning out the acoustic output signal 31 generated by the earpiece 18. Although the first embodiment of the telephone set 10 is most advantageous with two housings moveable relative to each other, the concept of porting the earpiece 18 through the keypad 20 may also be implemented in a telephone set having only one housing.

According to the second embodiment of the telephone set 10 as shown in FIG. 9 the microphone 16 is behind the keypad 20 in the first housing 12. The first housing 12 and the keypad 20 advantageously provides a large surface area to provide a privacy shield and acoustic coupling for the microphone 16 during voice conversations as well as to block wind and other noise from drowning out the acoustic input signal 26 generated by the person's mouth 65 for receipt by the microphone 16. Moreover, another advantage of the second embodiment of the telephone set 10 as shown in FIG. 9 is that the person's upper arm is permitted to rest comfortably alongside the person's torso to prevent fatigue in the person's arm during long voice conversations. Although the second embodiment of the telephone set 10 is most advantageous with two housings moveable relative to each other, the concept of porting the microphone 16 through the keypad 20 may also be implemented in a telephone set having only one housing.

What is claimed is:

1. A telephone set comprising:

a first housing;

a second housing;

an attachment mechanism coupled to the first housing and the second housing and adapted to permit the first housing to be moveable relative to the second housing between a first position and a second position;

a microphone carried by the first housing and adapted to convert an acoustic input signal into an electric input signal;

an earpiece carried by the second housing and adapted to convert an electric output signal into an acoustic output signal;

a display carried by the second housing; and a keypad carried by the second housing, wherein the keypad is disposed between the display and the microphone when the first housing is moved relative to the second housing to the second position, wherein the keypad has an inside surface disposed essentially opposite to an outside surface, the inside surface and the outside surface facing towards and away from, respectively, the second housing, wherein at least one of the outside surface of the keypad and the second housing is shaped to form a concave ear cup, wherein the keypad has a plurality of pushbutton keys arranged in a predetermined pattern, an outside edge of each of the plurality of pushbutton keys that is located near an outside edge of the predetermined pattern representing a perimeter of the keypad, wherein the keypad has an aperture extending through the keypad between the inside surface and the outside surface of the keypad, the aperture being disposed within the perimeter of the keypad and the aperture being disposed between the plurality of pushbutton keys, and wherein the earpiece faces the inside surface of the keypad and is disposed essentially opposite to the aperture of the keypad to permit the acoustic output signal generated by the earpiece to be ported through the aperture of the keypad.

2. A telephone set according to claim 1:

wherein the attachment mechanism is a rotate mechanism adapted to permit the first housing to rotate relative to the second housing between the first position and the second position, wherein the first position comprises a closed position, and wherein the second position comprises an open position.

3. A telephone set according to claim 1:

wherein the attachment mechanism is a slide mechanism adapted to permit the first housing to slide relative to the second housing between the first position and the second position, wherein the first position comprises a contracted position, and wherein the second position comprises an expanded position.

4. A telephone set according to claim 3:

wherein the first housing further comprises an elongated rod having a proximal end and a distal end, wherein the slide mechanism is a telescoping mechanism permitting the proximal end of the elongated rod to slide in and out of the second housing, and wherein the microphone is disposed at the distal end of the elongated rod.

5. A telephone set as in claim 4 wherein the elongated rod further comprises an antenna.

6. A telephone set according to claim 1 wherein the aperture is disposed along side one of the plurality of pushbutton keys.

7. A telephone set according to claim 1:

wherein the keypad further comprises a plurality of pushbutton keys, and wherein the telephone set is adapted to prevent accidental activation of the plurality of pushbutton keys by a person's ear or a person's head.

8. A telephone set according to claim 7 wherein the plurality of pushbutton keys are positioned to be substantially flush with the concave ear cup.

9. A telephone set as in claim 7:

wherein the plurality of pushbutton keys generate key input signals responsive to a predetermined measure of an actuation force, and wherein predetermined measure of the actuation force is provided more easily by a person's finger or other handheld object than by a person's ear or a person's head.

10. A telephone set according to claim 7 further comprising:
- a controller coupled to receive a plurality of key input signals generated by the plurality of pushbutton keys when the plurality of pushbutton keys actuated,
- wherein the controller disables the plurality of key input signals responsive to the controller detecting at least one of:
  - the ear cup being positioned proximate to the person's ear or the person's head,
  - the earpiece generating the acoustic output signal, and
  - the telephone set being engaged in a telephone call.

11. A telephone set according to claim 10:
- wherein the controller enables the plurality of key input signals responsive to the controller detecting at least one of:
  - the ear cup not being positioned proximate to the person's ear or the person's head,
  - the earpiece not generating the acoustic output signal, and
  - the telephone set not being engaged in a telephone call.

12. A telephone set according to claim 1 further comprising:
- a printed circuit board carried by the second housing,
- wherein the earpiece is carried between the printed circuit board and the keypad.

13. A telephone set according to claim 1 further comprising:
- a printed circuit board carried by the second housing,
- wherein the printed circuit board is carried between the earpiece and the keypad.

14. A telephone set comprising:
- a first housing forming an elongated rod having a proximal end and a distal end;
- a second housing;
- a telescoping mechanism coupled to the elongated rod and the second housing and adapted to permit the elongated rod to slide in and out of the second housing between a contracted position and an expanded position;
- a microphone carried by the distal end of the elongated rod and adapted to convert an acoustic input signal into an electric input signal;
- an earpiece carried by the second housing and adapted to convert an electric output signal into an acoustic output signal;
- a display carried by the second housing; and
- a keypad carried by the second housing,
- wherein the keypad is disposed between the display and the microphone when the elongated rod is moved relative to the second housing to the expanded position,
- wherein the keypad has an inside surface disposed essentially opposite to an outside surface, the inside surface and the outside surface facing towards and away from, respectively, the second housing,
- wherein at least one of the outside surface of the keypad and the second housing are shaped to form a concave ear cup,
- wherein the keypad has a plurality of pushbutton keys arranged in a predetermined pattern, an outside edge of each of the plurality of pushbutton keys that is located near an outside edge of the predetermined pattern representing a perimeter of the keypad,
- wherein the keypad has an aperture extending through the keypad between the inside surface and the outside surface of the keypad, the aperture being disposed within the perimeter of the keypad and the aperture being disposed between the plurality of pushbutton keys,
- wherein the telephone set is adapted to prevent accidental activation of the plurality of pushbutton keys when the outside surface of the keypad is placed against a person's ear or a person's head, and
- wherein the earpiece faces the inside surface of the keypad and is disposed essentially opposite to the aperture of the keypad to permit the acoustic output signal generated by the earpiece to be ported through the aperture of the keypad.

15. A telephone set as in claim 14 wherein the elongated rod further comprises an antenna.

16. A telephone set according to claim 14 wherein the aperture is disposed along side one of the plurality of pushbutton keys.

17. A telephone set according to claim 14 wherein the plurality of pushbutton keys are positioned to be subsantially flush with the concave ear cup.

18. A telephone set as in claim 14:
- wherein the plurality of pushbutton keys generate key input signals responsive to a predetermined measure of an actuation force, and
- wherein predetermined measure of the actuation force is provided more easily by a person's finger or other handheld object than by a person's ear or a person's head.

19. A telephone set according to claim 14 further comprising:
- a controller coupled to receive a plurality of key input signals generated by the plurality of pushbutton keys when the plurality of pushbutton keys actuated,
- wherein the controller disables the plurality of key input signals responsive to the controller detecting at least one of:
  - the ear cup being positioned proximate to the person's ear or the person's head,
  - the earpiece generating the acoustic output signal, and
  - the telephone set being engaged in a telephone call.

20. A telephone set according to claim 19:
- wherein the controller enables the plurality of key input signals responsive to the controller detecting at least one of:
  - the ear cup not being positioned proximate to the person's ear or the person's head,
  - the earpiece not generating the acoustic output signal, and
  - the telephone set not being engaged in a telephone call.

21. A telephone set according to claim 14 further comprising:
- a printed circuit board carried by one of the first housing and the second housing,
- wherein one of the microphone and the earpiece is carried between the printed circuit board and the keypad.

22. A telephone set according to claim 14 further comprising:
- a printed circuit board carried by one of the first housing and the second housing,
- wherein the printed circuit board is carried between one of the microphone and the earpiece and the keypad.

23. A telephone set comprising:
- a first housing;
- a second housing;

an attachment mechanism coupled to the first housing and the second housing and adapted to permit the first housing to be moveable relative to the second housing between a first position and a second position;

a microphone carried by the first housing and adapted to convert an acoustic input signal into an electric input signal;

an earpiece carried by the second housing and adapted to convert an electric output signal into an acoustic output signal;

a display carried by the first housing; and a keypad carried by the first housing, wherein the display is disposed between the keypad and the earpiece when the first housing is moved relative to the second housing to the second position, wherein the keypad has an inside surface disposed essentially opposite to an outside surface, the inside surface and the outside surface facing towards and away from, respectively, the first housing, wherein the keypad has a plurality of pushbutton keys arranged in a predetermined pattern, an outside edge of each of the plurality of pushbutton keys that is located near an outside edge of the predetermined pattern representing a perimeter of the keypad, wherein the keypad has an aperture extending through the keypad between the inside surface and the outside surface of the keypad, the aperture being disposed within the perimeter of the keypad and the aperture being disposed between the plurality of pushbutton keys, and wherein the microphone faces the inside surface of the keypad and is disposed essentially opposite to the aperture of the keypad to permit the acoustic input signal to be ported through the aperture of the keypad to be received by the microphone.

24. A telephone set according to claim 23:

wherein the attachment mechanism is a rotate mechanism adapted to permit the first housing to rotate relative to the second housing between the first position and the second position, wherein the first position comprises a closed position, and wherein the second position comprises an open position.

25. A telephone set according to claim 23:

wherein the attachment mechanism is a slide mechanism adapted to permit the first housing to slide relative to the second housing between the first position and the second position, wherein the first position comprises a contracted position, and wherein the second position comprises an expanded position.

26. A telephone set according to claim 25:

wherein the second housing further comprises an elongated rod having a proximal end and a distal end, wherein the slide mechanism is a telescoping mechanism permitting the proximal end of the elongated rod to slide in and out of the second housing, and wherein the earpiece is disposed at the distal end of the elongated rod.

27. A telephone set as in claim 26 wherein the elongated rod further comprises an antenna.

28. A telephone set according to claim 23 wherein the aperture is disposed along side one of the plurality of pushbutton keys.

29. A telephone se t according to claim 23:

wherein the keypad further comprises a plurality of pushbutton keys, and wherein the telephone set is adapted to prevent accidental activation of the plurality of pushbutton keys by a person's mouth or a person's head.

30. A telephone set according to claim 29 wherein the plurality of pushbutton keys are positioned to be substantially flush with the first housing.

31. A telephone set as in claim 29:

wherein the plurality of pushbutton keys generate key input signals responsive to a predetermined measure of an actuation force, and wherein predetermined measure of the actuation force is provided more easily by a person's finger or other handheld object than by a person's mouth or a person's head.

32. A telephone set according to claim 29 further comprising:

a controller coupled to receive a plurality of key input signals generated by the plurality of pushbutton keys when the plurality of pushbutton keys actuated, and wherein the controller disables the plurality of key input signals responsive to the controller detecting at least one of:

the first housing being positioned proximate to the person's head, the is microphone receiving the acoustic input signal, and the telephone set being engaged in a telephone call.

33. A telephone set according to claim 32:

wherein the controller enables the plurality of key input signals responsive to the controller detecting at least one of:

the first housing not being positioned proximate to the person's head, the microphone not receiving the acoustic output signal, and the telephone set not being engaged in a telephone call.

34. A telephone set according to claim 23 further comprising:

a printed circuit board carried by the first housing, wherein one of the microphone is carried between the printed circuit board and the keypad.

35. A telephone set according to claim 23 further comprising:

a printed circuit board being carried by the first housing, wherein the printed circuit board is carried between the microphone and the keypad.

* * * * *